(12) United States Patent
Bucourt et al.

(10) Patent No.: US 7,255,442 B2
(45) Date of Patent: Aug. 14, 2007

(54) DEVICE FOR MEASURING ABERRATIONS IN AN EYE-TYPE SYSTEM

(75) Inventors: Samuel Henri Bucourt, Bures sur Yvette (FR); Jean-Frances Xavier Levecq, Gif sur Yvette (FR)

(73) Assignee: Imagine Eyes, Orsay (FR)

( * ) Notice: Subject to any disclaimer, the term of this patent is extended or adjusted under 35 U.S.C. 154(b) by 727 days.

(21) Appl. No.: 10/486,664

(22) PCT Filed: Aug. 12, 2002

(86) PCT No.: PCT/FR02/02859

§ 371 (c)(1),
(2), (4) Date: Feb. 12, 2004

(87) PCT Pub. No.: WO03/015622

PCT Pub. Date: Feb. 27, 2003

(65) Prior Publication Data

US 2004/0189941 A1 Sep. 30, 2004

(30) Foreign Application Priority Data

Aug. 12, 2001 (FR) .................................. 01 11112

(51) Int. Cl.
*A61B 3/10* (2006.01)
(52) U.S. Cl. ..................................... 351/221; 351/213
(58) Field of Classification Search ................ 351/205, 351/212–221
See application file for complete search history.

(56) References Cited

U.S. PATENT DOCUMENTS 5,777,719 A * 7/1998 Williams et al. ............ 351/212

| | | | |
|---|---|---|---|
| 6,050,687 A | 4/2000 | Bille et al. ................... | 351/212 |
| 6,086,204 A | 7/2000 | Magnante .................... | 351/212 |
| 6,264,328 B1 | 7/2001 | Williams et al. ............ | 351/221 |
| 6,409,345 B1 * | 6/2002 | Molebny et al. ............ | 351/212 |
| 2005/0007551 A1 * | 1/2005 | Wakil et al. ................. | 351/205 |

OTHER PUBLICATIONS

Liang J et al: "Objective Measurement of Wave Aberrations of the Human Eye With the use of a Hartmann-Shack Wave-Front Sensor", Journal of the Optical Society of America, American Institute of Physics. New York, US, vol. 11, No. 7, Jul. 1994, pp. 1949-1957, XP000955413 cited in the application the whole document.

* cited by examiner

*Primary Examiner*—Hung Dang
*Assistant Examiner*—M. Hasan
(74) *Attorney, Agent, or Firm*—Young & Thompson

(57) ABSTRACT

Device for measuring aberrations in an eye includes, an illumination path with an illumination diaphragm and a test path, imaging member and elements for positioning the eye in relation to the imaging member, a stray reflection filter element, which is centered on the measurement axis of the imaging member, and elements for the optical conjugation of the pupil of the eye with the plane of the illumination diaphragm and the test plane. The illumination beam path converges at the center of the filtration element. The filtration element, the illumination path, the test path and the conjugation elements are all interdependent and positioned on a platform that can move in relation to the imaging member along the axis. The illumination diaphragm is off-center in relation to the axis such that stray light flux reflected by the imaging member is deflected from the test path by filtration element.

21 Claims, 9 Drawing Sheets

DEVICE FOR MEASURING ABERRATIONS IN AN EYE-TYPE SYSTEM

The invention relates to a device for measuring aberrations in an eye-type system, living eye or artificial eye, fitted or not with corrective lenses, the result of these measurements enabling notably to define with accuracy vision corrective optical elements, to contribute to corrective eye surgery, to detect ocular pathologies, and more generally to provide accurate measurements to any apparatus requiring perfect knowledge of eye aberrations. The device according to the invention also enables to establish the topography of the front face of the cornea.

Most instruments used today by optometrists for correcting ocular vision only measure ametropia (myopia or hypermetropia) and astigmatism. They cannot measure all the eye aberrations, in particular coma, spherical aberration or higher level aberrations, involving approximate correction of vision.

Recently, devices for measuring eye aberrations have been developed, based upon the use of a Shack-Hartmann type wave-front analyser (see for example 'Objective measurement of wave aberrations of the human eye with the use of Shack-Hartmann wave-front sensor', Liang et al., J. Opt. Soc. Am. A., Vol. 11, no 7, pages 1-9, 1994). In such a device, the wave-front analyser enables to analyse the wave emerging from the eye after focusing on the retina of an illumination beam, thereby generating a diffusing source point. The performances obtained are however limited by stray reflections, on the cornea and on the optical elements of the assembly, which cause inaccuracies in the wave-front analysis. The assembly recommended by Williams et al. (U.S. Pat. No. 0,577,719) solves partially the problem of stray reflections by using a biasing separating blade.

However, it is important in a device of such a type to optimize the light output between the flux penetrating the eye and the flux which may be collected in order to perform the wave-front analysis, in order to limit, for the patient's comfort, the light flux incident on the retina. Still, the use of a biasing separating blade as recommended in the patent aforementioned, causes significant flux loss on the analysis path.

To remedy this shortcoming in particular, the invention provides a device for measuring aberrations in an eye-type system, comprising a wave-front analyser, for example of Shack-Hartmann type, which optimizes the light output between the flux incident on the retina and the flux collected for analysis, while providing very high measurement reliability and easy optical assembly.

To do so, the device according to the invention comprises an illumination path with notably means for transmitting an illumination beam to form by backscattering on the retina of the eye a secondary light source and an analysis path with notably test means in a given analysis plane of the phase of the wave emitted by said secondary source and emerging from the eye, characterised in that it further comprises:

imaging means and eye-positioning means enabling in particular to position a predetermined plane of the eye in a focal plane of said imaging means, a stray reflection filtering element whereof the centre defines with the optical centre of the imaging means a measurement axis, substantially centred on the pupil of the eye, optical separation means placed on the measurement axis and defining the illumination path and the analysis path, on the illumination path, an illumination diaphragm, of predetermined aperture, optical conjugation means centred on the measurement axis and enabling optical conjugation between said predetermined plane of the eye, the plane of the illumination diaphragm and the analysis plane, and characterised in that the illumination beam converges substantially at the centre of the filtering element, in that the filtering element, the illumination path, the analysis path, the separation means and the conjugation means are interdependent, placed on a platform mobile relative to the imaging means along the optical axis of said means, enabling adjustment, with respect to the ametropia of the eye, of the optical conjugation by said means of the retina of the eye with the centre of the filtering element, and in that the illumination diaphragm is off-centre with respect to the measurement axis, so that the stray light flux reflected by the cornea of the eye, the imaging means as well as any diopter situated between the filtering element and the cornea, is deflected from the analysis path by the filtering element.

Other advantages and features of the invention will appear more clearly when reading the following description, illustrated by the figures wherein.

Figure 1A:
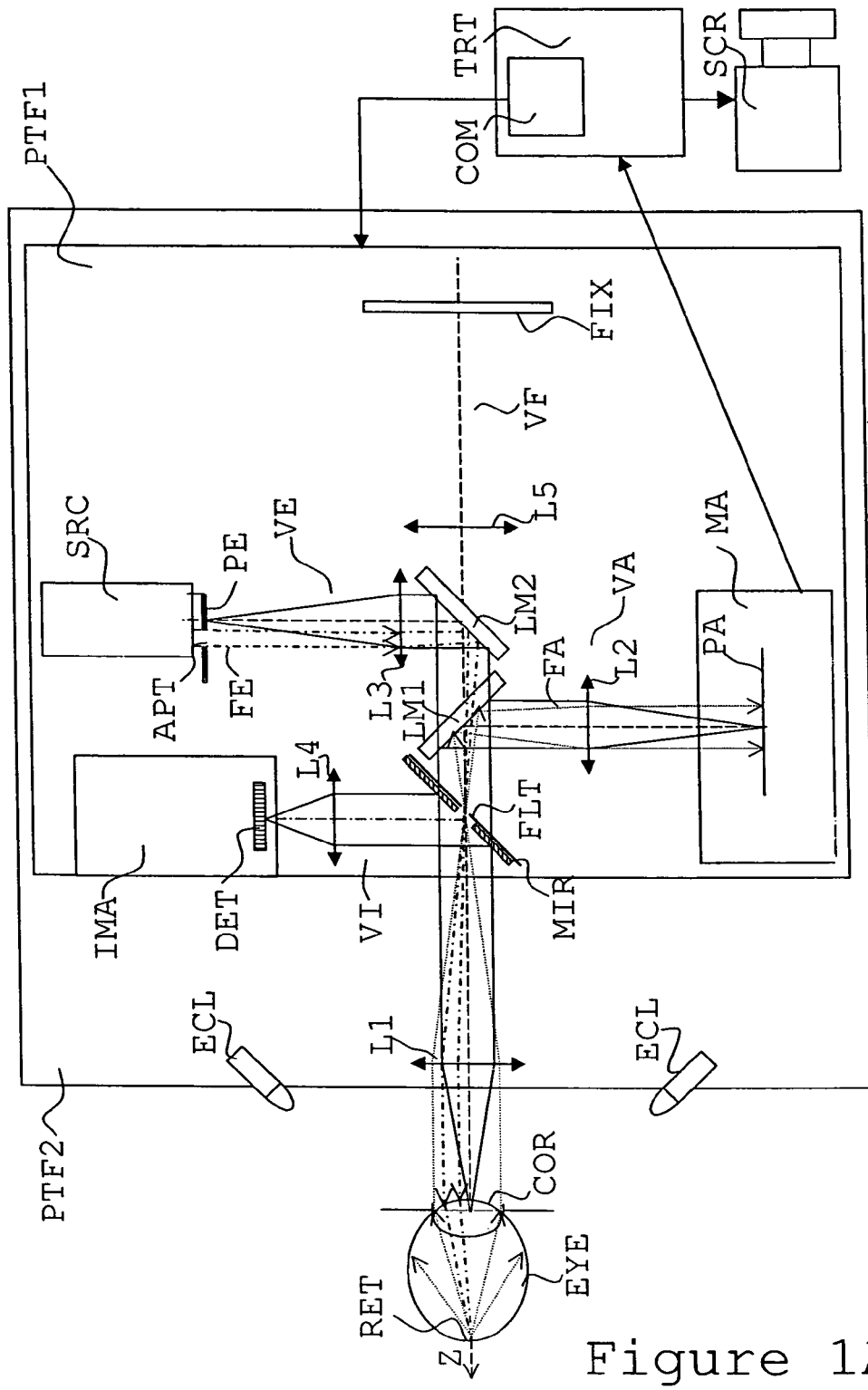
FIGS. 1A and 1B, show assembly examples illustrating the device of the invention according to a first variation.
Figure 5:
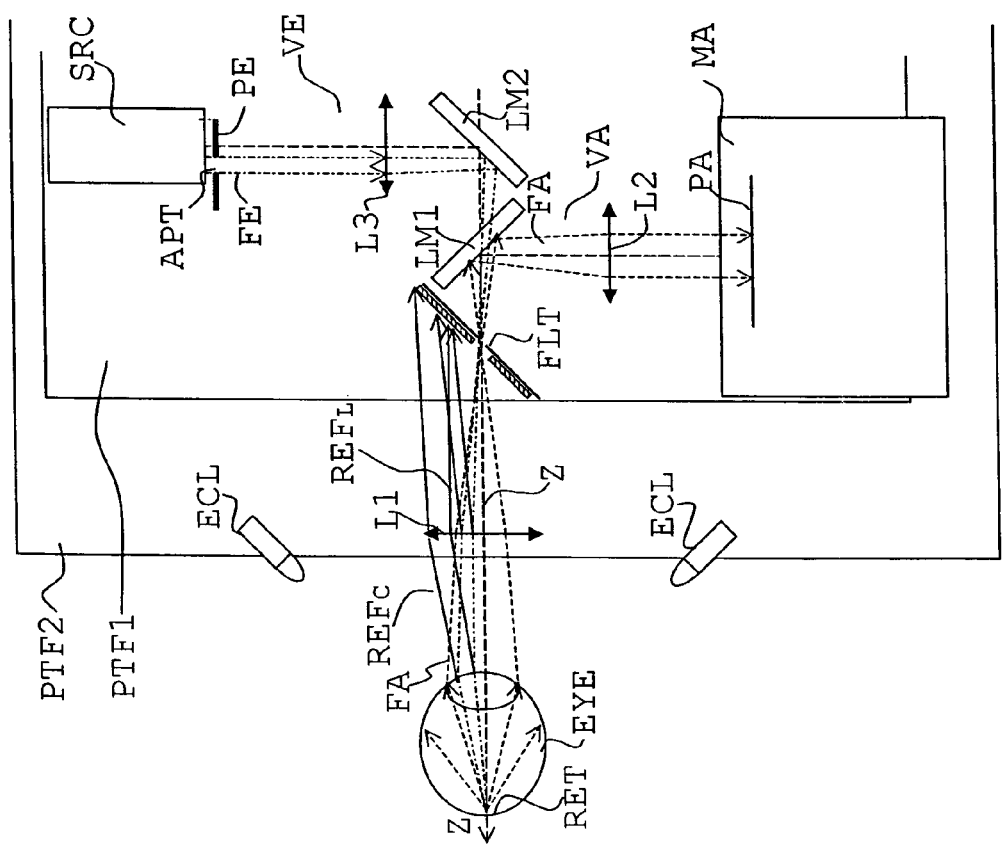
Figure 6:
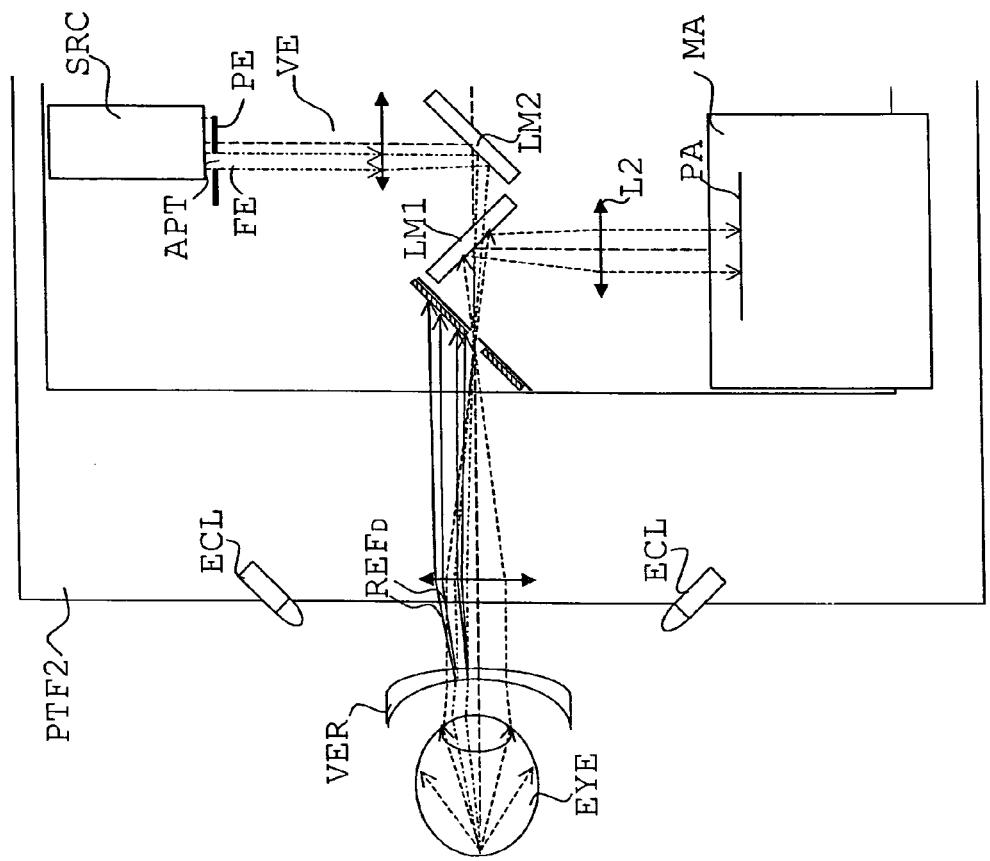
Figure 7:
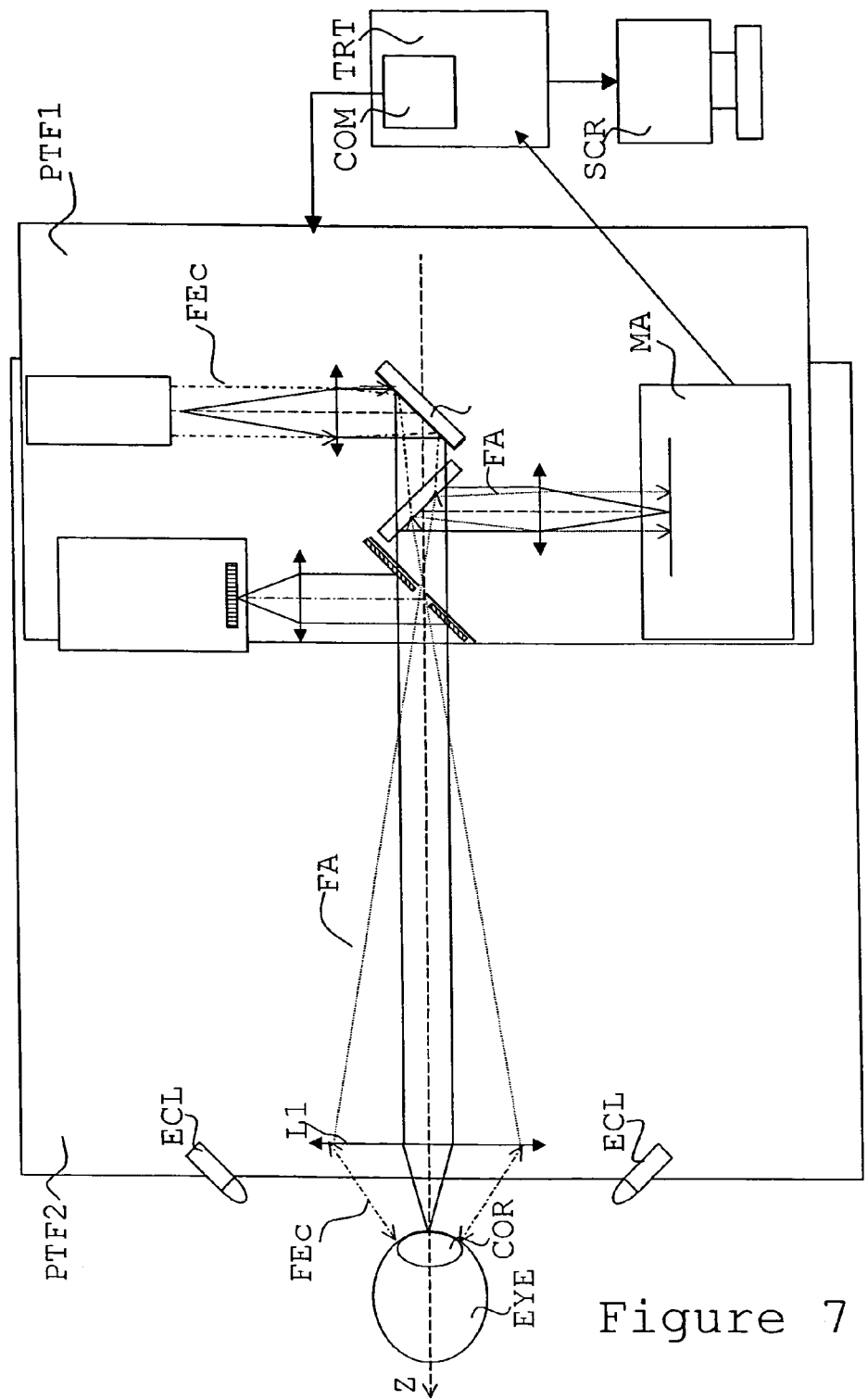
Figure 8:
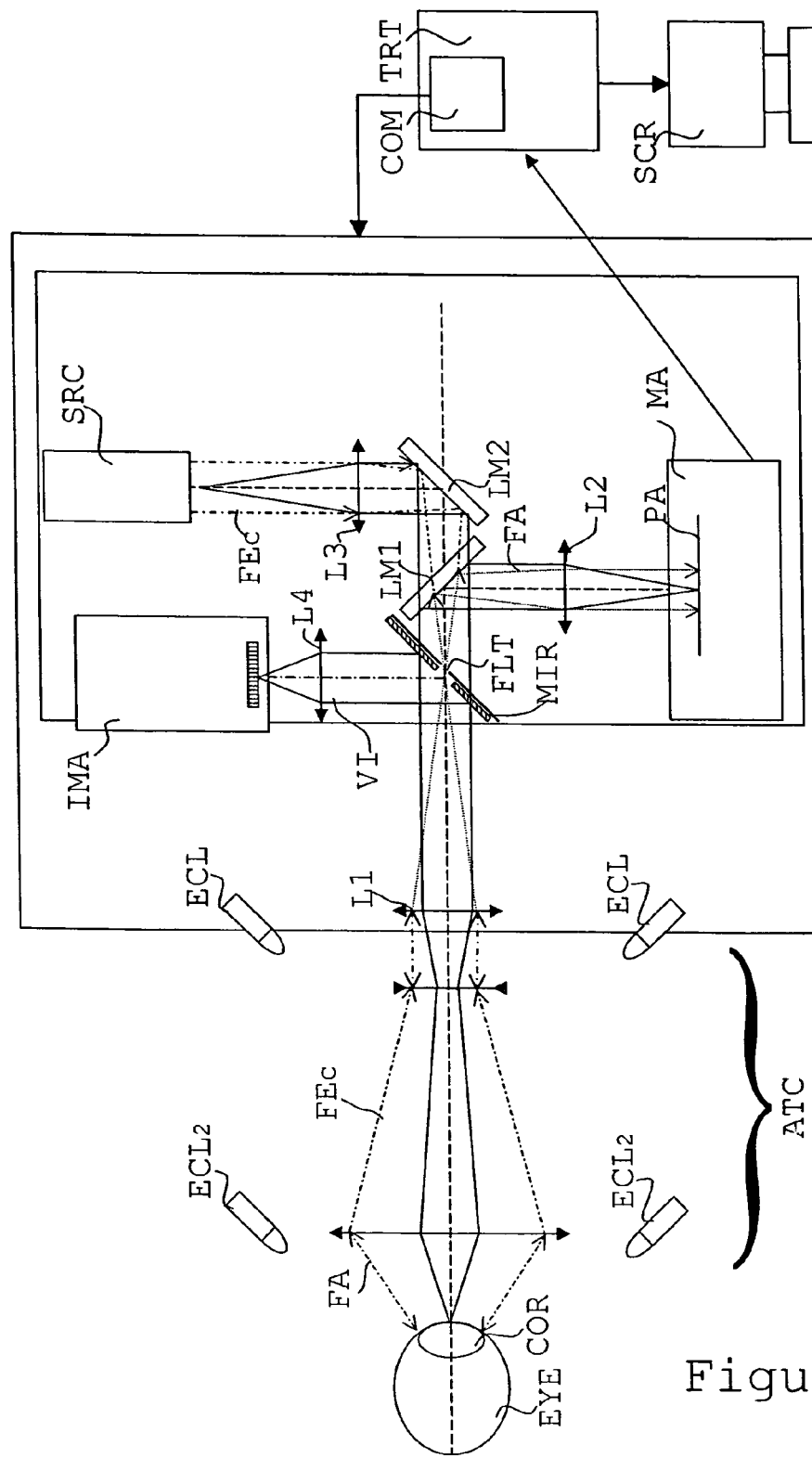

FIG. 5 underlines the stray reflections in the assembly described on FIG. 1A;

FIG. 6 underlines the stray reflections in the case of patient wearing corrective lenses;

FIG. 7 is a diagram illustrating the application of the device according to the invention to cornea topography;

FIG. 8 is a diagram illustrating an embodiment of the device for application to cornea topography measurement.

On these Figures, the identical elements are indicated by the same references.

Figure 1B:
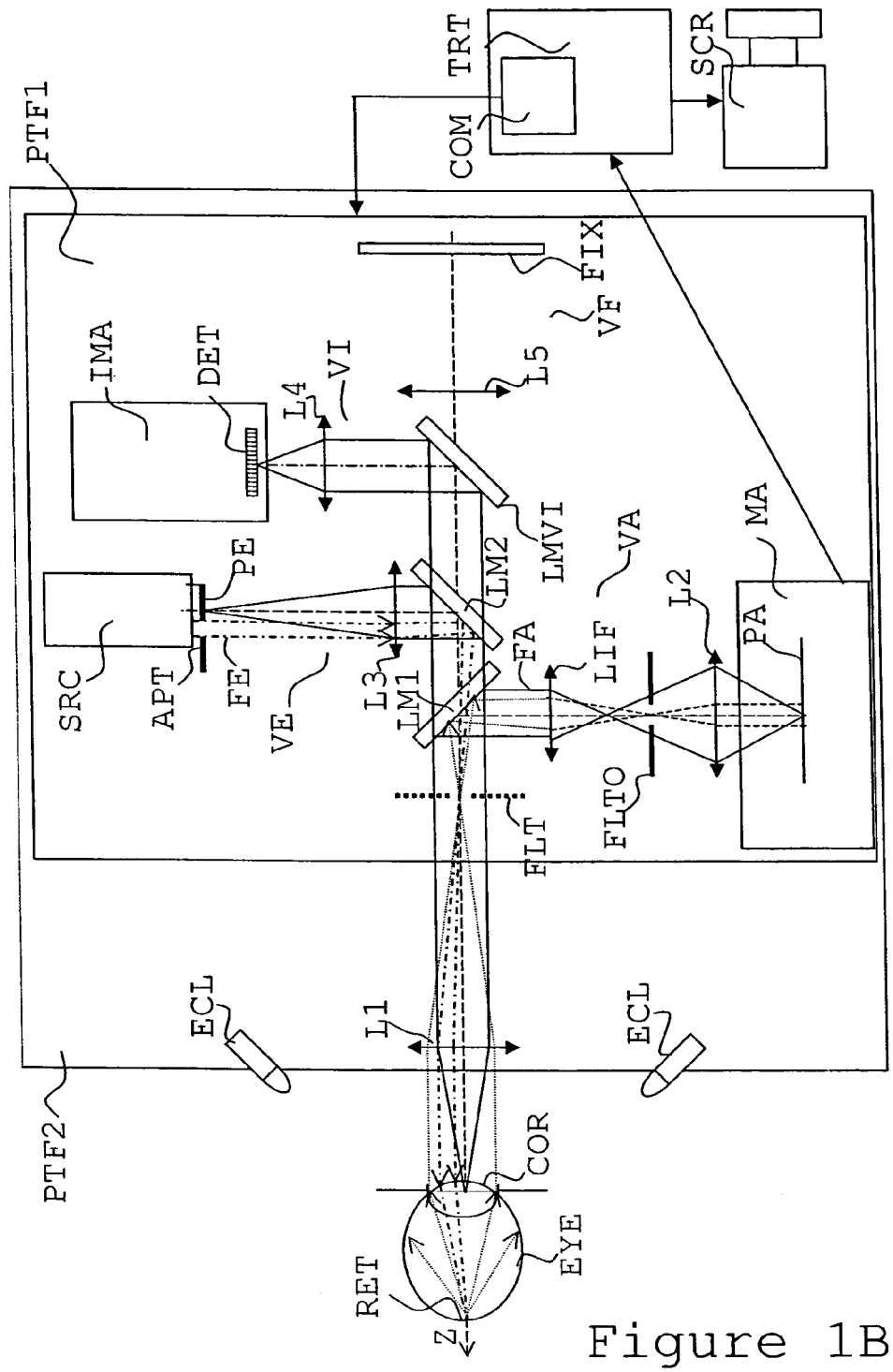
Figure 2:
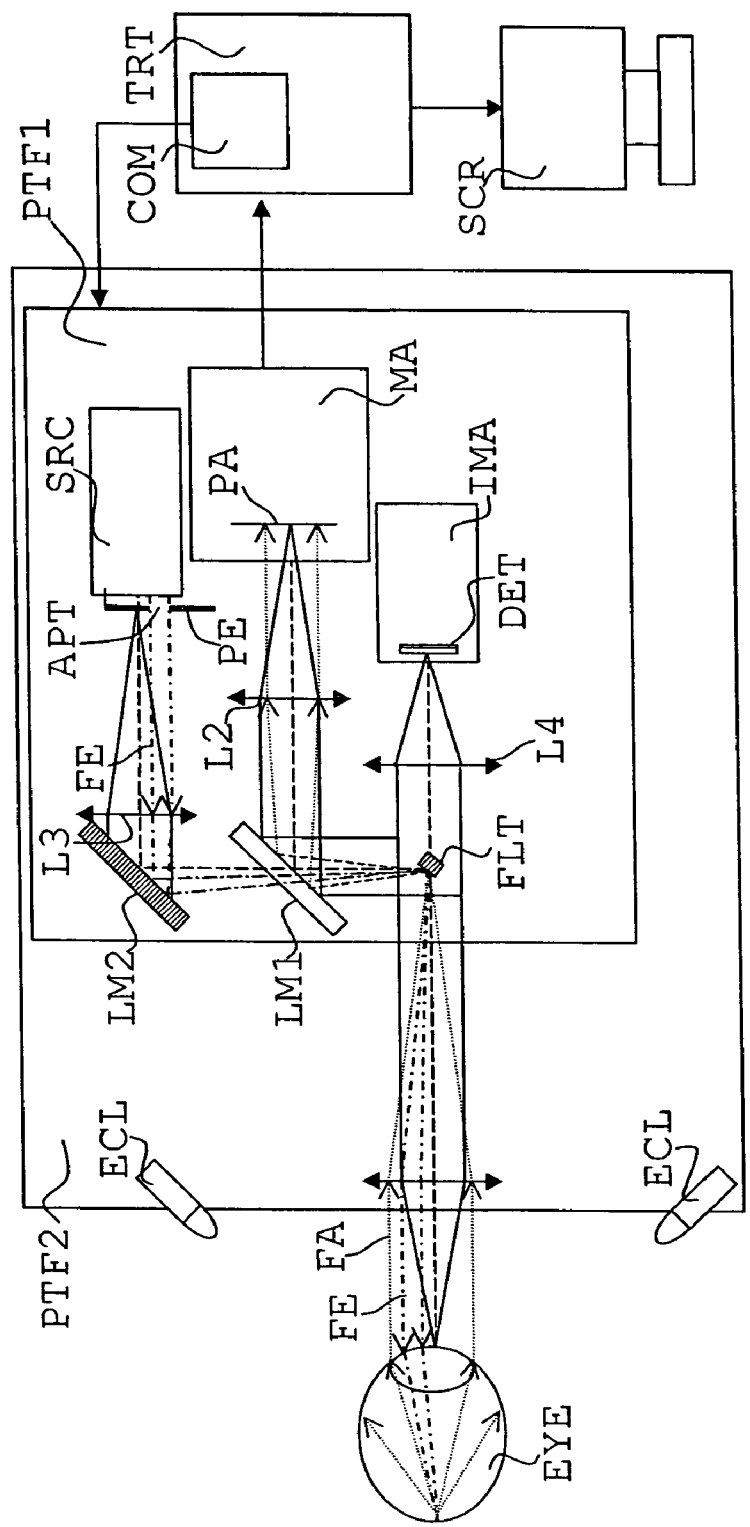
FIG. 2 is an assembly example illustrating the device of the invention according to a second variation.

FIGS. 1A, 1B and 2 represent assembly examples illustrating the device for measuring aberrations in an eye-type system according to the invention.

The device comprises conventionally an illumination path VE with notably means SRC for transmitting an illumination beam FE (represented by a mixed dotted line on FIGS. 1A and 1B) in order to form on the retina RET of the eye to be tested EYE a diffusing light source point. It further comprises an analysis path VA with in particular optical analysis means MA in a given analysis plane PA of the wave-front phase emitted by said source point and emerging from the eye (beam FA represented as a dotted line on FIGS. 1A and 1B). The analysis means, for example a Shack-Hartmann type analyser, are connected to processing means TRT which, in a known fashion, map the phase of the wave emerging from the eye and calculate the aberrations. A representation of this map can be displayed on a screen SCR. The operation of the Shack-Hartmann analyser, known from the previous art (see for example the article "wave-front estimation from wave-front slope measurements", J. Opt. Soc. Am. Vol. 70, no. 8, August 1980), is not detailed further herein. More simply, it comprises usually a matrix of microlenses, defining the analysis plane PA, and a matrix sensor. Each of the microlenses forms on the sensor an image point of the portion of the wave-front that it intercepts. The aberrations of the wave emerging from the eye (beam FA) cause the image points on the sensor to move over a distance proportional to the focal slope of the wave-front. The signal generated by the sensor is sent to the processing means TRT which map the phase of the wave-front, thereby enabling to deduce therefrom the aberrations of the eye thus analysed. It should be noted, however, that the invention is not limited to the use of the Shack-Hartmann analyser and that other wave-front analysers enabling phase mapping of a wave-front may also be considered.

One of the difficulties encountered in such a device comes from the elimination of the stray reflections on the different diopters of the assembly. Indeed, the flux diffused by the retina and emerging from the eye is very small and spurious stray reflections involve generally saturation of the image which renders any analysis impossible. Besides, it is important to optimize the light output between the flux incident on the retina and the flux emerging from the eye after diffusion on the retina in order to reduce the quantity of light flux penetrating the eye of the patient. The device implemented by the applicants and whereof the embodiments are represented on FIGS. 1A, 1B and 2, reconciles these constraints while providing an easy assembly, with very good measurement reliability.

To do so, the device according to the invention comprises imaging means, for example a lens L1, and eye-positioning means enabling in particular to position a predetermined plane of the eye, for example the plane of the pupil of the eye PO, or the plane tangent to the apex of the cornea in a focal plane of the lens L1. It further comprises a stray reflection filtering element FLT whereof the centre defines with the optical centre of the imaging means L1 a measurement axis, noted z, and represented as a long dotted line. The measurement axis is substantially centred on the pupil of the eye. It also comprises optical separation means positioned on the measurement axis and defining the illumination path VE and the analysis path VA. On the examples of FIGS. 1A, 1B and 2, the separation means are placed upstream of the filtering means FLT and composed of a first blade LM1 which reflects the analysis beam FA from the eye to the analysis means and of a second blade LM2 which defines the illumination path VE. It also includes, on the illumination path, an illumination diaphragm APT and optical conjugation means, centred on the measurement axis, and ensuring optical conjugation between the pupil of the eye PA, the plane of the illumination diaphragm PE and the analysis plane PA. On the simple example of FIGS. 1A and 2, these conjugation means are provided by two lenses, L2 and L3, placed respectively on the analysis path VA and the illumination path VE. The plane of the illumination diaphragm PE is confused with a focal plane of L3 and the analysis plane is confused with a focal plane of L2, thereby enabling conjugation of the pupil of the eye PO with the planes PE and PA. On the example of FIG. 1B, the conjugation of the illumination diaphragm PE with the pupil of the eye is identical to the cases of FIGS. 1A and 2. Conversely, the conjugation between the analysis plane PA and the pupil of the eye is carried out by both lenses LIF and L2, the analysis plane PA being placed at the focus of the optical system formed by both lenses LIF and L2.

According to the invention, the illumination beam FE converges at the centre of the filtering element FLT. On the example of FIGS. 1A, 1B and 2, the lens L3 enables to focus the illumination beam at the centre of the filtering element FLT. For instance, the transmission means SRC are composed of a collimated laser diode and the filtering element FLT is situated at the focus of the lens L3. Moreover, the filtering element FLT, the illumination path VE, the analysis path VA, the separation means LM1, LM2 and the conjugation means L2, L3 are interdependent, placed on a platform PTF1 mobile along the measurement axis (z) with respect to the imaging means L1. Besides, according to the invention, the illumination diaphragm APT, for example a circular aperture diaphragm of predetermined diameter, is off-centre with respect to the measurement axis z so that the stray light flux reflected by the cornea of the eye, the imaging means (L1) and any diopter situated between the filtering element and the cornea, is deflected from the analysis path by the filtering element (FLT).

According to the variation described, illustrated on FIG. 1A, the filtering element FLT is composed of a drilled opaque blade, in this example a mirror, the hole being centred on the measurement axis, of predetermined dimensions so that the illumination beam FE and the analysis beam FA focused at the centre of said hole, are transmitted by the filtering element whereas the stray reflections are stopped by the opaque portion of the filtering element. According to a variation, the size of the hole of the opaque blade is controllable. A small-sized hole enables very good insulation against the stray reflections formed by any diopter situated between the filtering element and the cornea, in particular when the patient is equipped with corrective lenses whereof the curvature radii may be small. Conversely, if the eye measured is not fitted with corrective lenses and shows a high level of astigmatism or a pathology of keratoconus type, for example, the measurement dynamics of the aberration measuring system should not, preferably, be limited by too small a filtering element. In such a case, the size of the hole of the filtering element can be enlarged in order to increase the dynamics of the measurement. Besides, according to the invention and as represented on FIG. 1B, the filtering element FLT can be a virtual element (represented in dotted lines), an image of the actual filtering element FLTO by the optical element LIF. The functionalities of this variation are identical to those exposed on FIGS. 1A and 2. The function fulfilled by the lens L2 in the case of FIGS. 1A and 2, is carried out by the optical system formed by the couple of lenses LIF and L2 in the case of FIG. 1B. The only difference is that the actual filtering element FLTI is situated on the analysis path VA and the filtering element FLT is the image of the actual filtering element FLTO formed by the lens LIF. The advantage of this variation is that it is easier to insert a filtering element of controllable size on the plane of FLTO than on the plane of FLT. On the example of FIG. 2, the filtering element FLT comprises a mirror centred on the measurement axis, of predetermined dimensions so that the illumination beam FE and the analysis beam FA focused at the centre of said mirror are reflected by the filtering element whereas the stray reflections are not deflected by said element.

The features described above enable to optimize, in a compact assembly, showing a few optical elements, the performances of the eye aberration measurement device. The conjugation of the pupil of the eye PO with the plane of the illumination diaphragm PE and the analysis plane PA, is specified on FIGS. 1A, 1B and 2 as a full line. This conjugation enables on the one hand, regardless of the ametropia of the eye, constant diameter of the illumination zone on the eye, enabling perfect control of the incident flux in the eye and, on the other hand, the size of the zone illuminated on the analysis plane PA to be directly representative of the position and of the shape of the pupil of the eye, in front of L1, there again regardless of the ametropia of the eye. Means for positioning the pupil of the eye PO on a focal plane of the lens L1 are required accordingly; they will be described below.

Translation adjustment of the platform PTF1 along the measurement axis z enables, relative to the ametropia, optical conjugation by the lens L1 of the retina of the eye RET with the centre of the filtering element FLT. It is essential in the device according to the invention that the filtering element FLT, the illumination path VE, the analysis path VA, the separation means (LM1, LM2) and the conjugation means (L2, L3) are interdependent during the displacement of the platform PTF1. Indeed, this enables to maintain constant the relative positions of the illumination diaphragm and of the analysis plane with the filtering element regardless of the position thereof, to provide thereby fixed measuring conditions, which guarantees the reliability of the measurement. In the example of FIGS. 1A and 2, the filtering element FLT lies substantially at the focus of L2 so that the analysis beam FA arrives substantially collimated on the analysis plane PA. In the case of FIG. 1B, the filtering element FLT, the image of the actual filtering element FLTO by the lens LTF, is substantially at the focus of the optical system of the analysis path VA (formed by the couple of lenses LIF and L2) so that the analysis beam FA arrives substantially collimated on the analysis plane PA.

FIGS. 1A, 1B and 2 represent, according to an example, the plot of the illumination beam FE and of the analysis beam FA in the case of an emmetropic eye. The beam emerges collimated from the transmission means, formed for instance of a laser diode transmitting in the visible or near infrared range. The illumination diaphragm limits the light beam to an illumination beam FE of predetermined diameter, off-centre with respect to the measurement axis. The lens L3 focuses the beam FE at the centre of the filtering element FLT which, in this sense has no incidence on the light beams. After the focusing point, the beam diverges and reaches the lens L1. In the case of an emmetropic eye ('O dioptry' position of the platform PTF1), the focusing point at the focus of L3 (centre of the filtering element) is at the focus of L1. The incident beam on L1 lies outside the optical axis taking into account the eccentric position of the illumination diaphragm, thus, the reflection on L1 (not represented) does not come back following the same direction; it is reflected by the drilled mirror in the variation of FIG. 1A, it is stopped by the filtering element FLT in the case of FIG. 1B and it is, conversely, not deflected in the example of FIG. 2 where the filtering element is a small, centred, mirror. At the output of L1, the beam is collimated and reaches the pupil of the eye on an image plane of the illumination diaphragm. As the latter is eccentric, its image on the pupil is also eccentric and the reflection (not represented) on the cornea COR of the eye, highly vaulted, is blocked by the filtering element. The beam enters the eye and it is focused on the retina RET. The selection of the diameter of the illumination diaphragm enables to optimize, taking into account the aberrations of the eye, the size of the focusing point on the retina.

The retina is a diffusing object. Light beams are reflected from the point of impact of the light beams incident on the retina. The light spot on the retina is used as a secondary illumination source for the analysis means of the wave-front. The phase of the wave diffused by the retina is spherical. From this secondary illumination source, the beam goes through the eye, 'records' the aberrations and a portion of the beam comes out of the eye through the pupil PO forming the analysis beam FA. In the case of an emmetropic eye, the beam is globally collimated at the output of the eye (same vergence as the incident beam FE). This 'return' beam is focused at the focus of L1, at the centre of the filtering element FLT, where it is confused with the focusing point of the illumination beam FE. In the examples of FIGS. 1A and 2, the centre of the filtering element is at the focus of L2 (via the blade LM1). In the example of FIG. 1B, the centre of the filtering element lies substantially at the focus of the optical system formed by the lenses LIF and L2 (via the blade LM1). Thus, the beam tested by the analyser is globally collimated. The analyser measures the defects of the wave surface generated by the 'eye' system. The size of the zone illuminated on the analyser is proportional to the size of the pupil of the eye (within the enlargement factor, given by the focal ratio of the lenses L2 and L1 in the case of FIGS. 1A and 2).

Advantageously, the blade LM1, which transmits the 'out' illumination beam FE and reflects the 'back' analysis beam FA is a blade with flat and parallel faces, tilted approximately at 45° on the measurement axis, and whereof the reflection coefficient has been selected to optimize the light output. For instance, the reflection coefficient is greater than approximately than 70% in order to maximise the flux of the analysis beam (it is not cumbersome to have a low transmission coefficient, for example of the order of 10%, whereas the light power of the transmission means may be adjusted accordingly). This reflection configuration, advantageously, does not introduce any astigmatism on the analysis beam FA (on a non-collimated beam, during transmission, a blade with flat and parallel faces introduces astigmatism). It is also interesting to select the thickness of the blade M1 so that the offset introduced on the illumination beam with respect to the measurement axis z is such that, if the blade LM1 has been displaced, accidentally, causing sudden increase in the flux incident on the eye, the illumination beam is stopped (case of FIG. 1A) or not reflected towards the eye (case of FIG. 2) by the filtering element.

In the examples described above, the eye-positioning means comprise an imaging path VI of the pupil, with an imaging system IMA interdependent upon the platform PTF1, and including a detector DET situated on the focal plane of a lens L4. An illumination device ECL, for example composed of light-emitting diodes ECL, can be provided to illuminate the pupil of the eye. The position of the pupil is adjusted for instance by tuning the image of the pupil on the detector DET. Advantageously, the illumination device of the eye being formed of a set of light sources, the position can be adjusted by tuning the image of said sources reflected by the cornea on the detector, thereby enabling to control the position of the plane tangent to the apex of the cornea of the eye. Preferably, the position of this plane should be controllable, rather than the position of the plane of the pupil, since the ametropia of the eye is defined with respect to the apex of the cornea.

Figure 3:
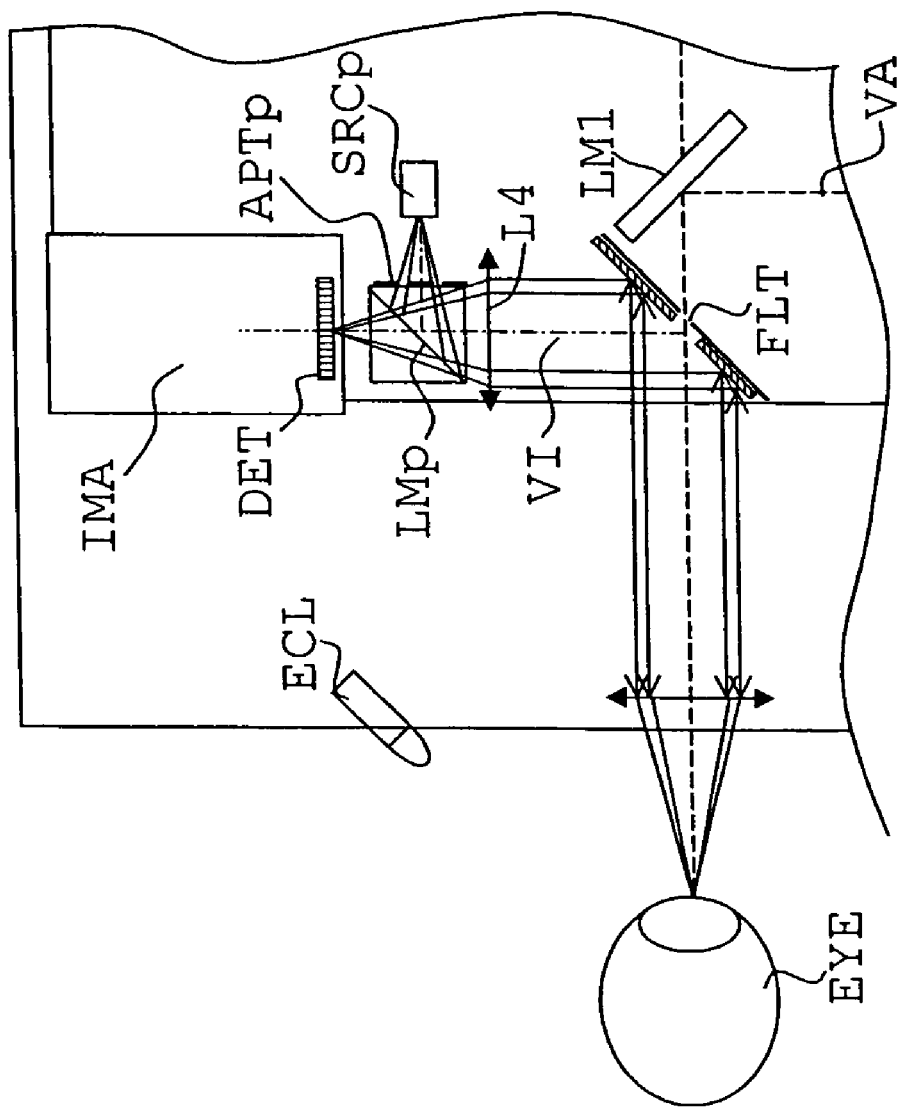
FIG. 3 is a diagram illustrating an embodiment of the eye-positioning means in the device according to the invention.

For further fine-tuning of the position adjustment of the plane tangent to the apex of the cornea with respect to the imaging means L1, it can be provided a positioning assistance system as described on FIG. 3. FIG. 3 details the assembly example described on FIG. 1A, but for simplicity purposes, only certain elements are represented. The positioning assistance system comprises a quasi-punctual light source $SRC_P$, centred on the measurement axis z, and placed substantially at the focus of the lens L4 of the imaging path, a mask formed of at least two apertures whereof at least one is off-centre with respect to the measurement axis, and located near said source, to form at least two light beams, and a separating blade $LM_P$ receiving said beams. Positioning is adjusted by controlling on the detector DET of the imaging path, the superimposition of the spots formed by the beams after reflection on the cornea of the eye, thus enabling controlled positioning of the plane tangent to the apex of the cornea of the eye. In this example, two beams are formed thanks to a double diaphragm $APT_P$ placed at the input of a separating cube (source side) whereof the separating face forms the separating blade. The source can be formed of a laser diode or of a light-emitting diode.

Figure 4:
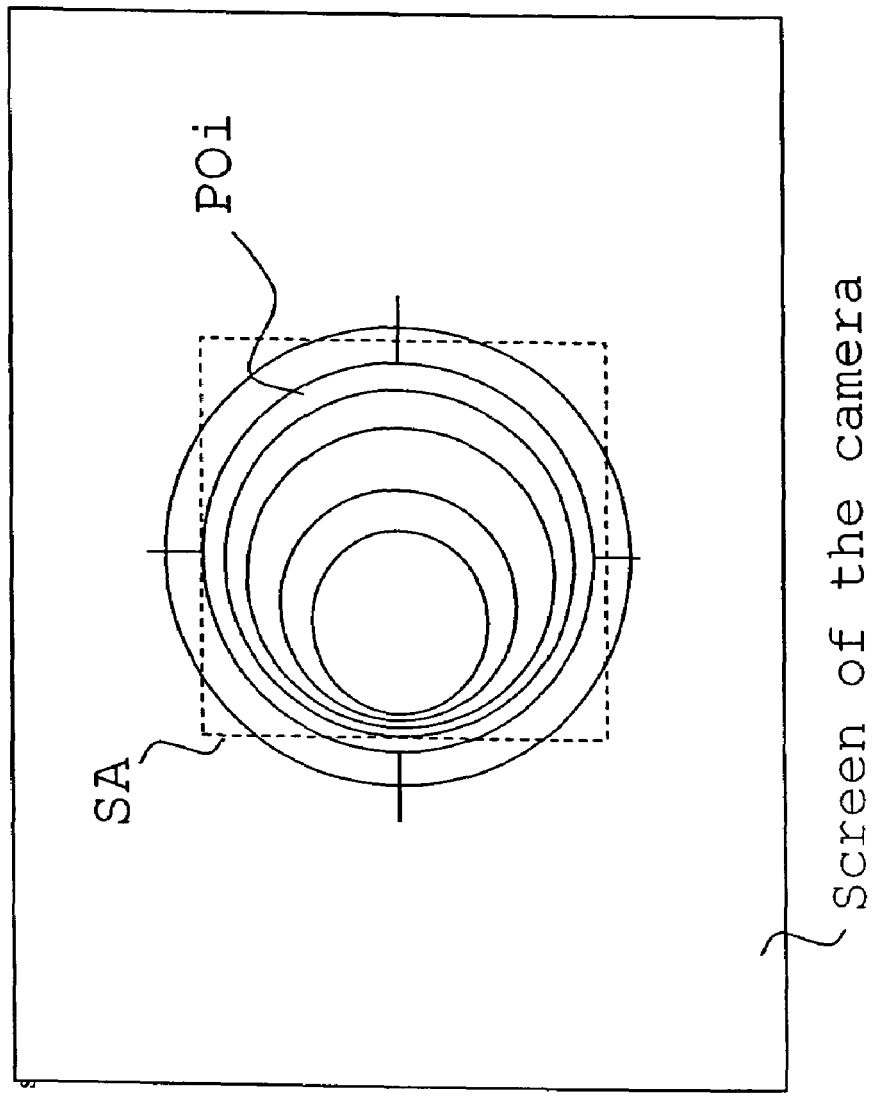
FIG. 4 is a diagram illustrating a prop for lateral positioning of the eye.

According to a variation, the eye-positioning means further comprise on the display of the camera of the imaging path, means for tracking the lateral position of the pupil of the eye, enabling to adjust this lateral position with respect to the position of the illumination beam relative to the size of the pupil. These tracking means, which appear for instance on the display of the camera of the imaging path, are represented, according to an example, on FIG. 4. The dotted square SA represents the useful of the analyser added-on in the plane of the imaging camera IMA of the imaging path VI (FIG. 1A or 2). The circles $PO_1$ represent the lateral positioning marks for pupils of different size. When the pupil of the eye is of significant size. (young subject or eye under mydriatic product), the pupil should be centred at best so that the surface covered on the analyser is optimum. Taking into account the great size of the pupil, there is no problem for the incident beam FE (on FIG. 1A or 2 for example), offset from the optical axis, to enter the pupil of the eye under study. Conversely, when the pupil of the eye is smaller (typically an aged eye), it should be taken off-centre so that the incident flux enters the eye.

Advantageously, the positioning means further comprise means for moving the imaging means L1 and the platform PTF1, interdependently, in order to adjust the positioning of the pupil. In the examples of FIGS. 1A, 1B and 2, the lens L1 and the platform PTF1 are mounted on a second platform PTF2, which can move in all directions.

In the example of FIG. 1A, the filtering hole FLT of the stray reflections is formed in a reflecting mirror MIR, tilted with respect to the measurement axis z by approximately 45°, sending towards the imaging path VI the light flux coming from the pupil PO. The use of the mirror MIR thus arranged dispenses in particular with adding any other blade through which the analysis beam would go. In the example of FIG. 2, the centred mirror lets through the light flux from the pupil PO towards the imaging path VI.

As can be seen on FIG. 1A for example, the device according to the invention may also comprise a fastening path VF, enabling to fix the patient's attention whereof the eye is tested, and including an illuminated image FIX forming a fastening target and a lens L5, the lens conjugating substantially the image with the filtering hole FLT (the plot of the beams is not represented on FIG. 1A for clarity purposes). Ideally, the fastening target is not perfectly conjugated with the filtering hole and the retina; the system should be adjusted so that said target is seen with slight myopic out-of-focus which stimulates dis-accomodation.

Practically, the aberration measurement protocol with the device according to the invention can be as follows. If the patient knows his ametropia approximately (he is either short-sighted, long-sighted or emmetropic), one adjusts the position of the platform PTF1 on approximately 2 dioptries above the ametropia announced so that the patient cannot compensate (for an emmetropic eye, the platform PTF1 is adjusted for example on '+2 dioptries', i.e. the filtering hole FLT is situated at sufficient distance from the lens L1 to conjugate the retina and the filtering hole by L1 in case when the eye shows 2-dioptry hypermetropia). Thanks to the imaging camera IMA of the imaging path VI, the position of the platform PTF2 is adjusted with respect to the eye in order to conjugate for example the plane tangent to the apex of the cornea of the eye PO with the plane of the illumination diaphragm PE and the analysis plane PA. A first measurement with the wave-front analysis means enables to determine on the wave-front the global out-of-focus on the analysis beam. Advantageously, the device according to the invention comprises moreover means COM for controlling the platform PTF1, connected to the analysis means MA and enabling to control the displacement along the measurement axis z of the platform PTF1. The control means receive from the processing means TRT the value of the global out-of-focus on the analysis beam arid may control the displacement of the platform PTF1 accordingly, so that the retina of the eye is conjugated with the filtering element FLT by the lens L1. The value of this displacement with respect to an origin position enables to determine with precision the actual ametropia of the eye. The aberrations are then measured. It is advisable to adjust the platform PTF1 during this measurement to a position corresponding to a few fractions of dioptry above the actual ametropia of the eye so that the patient will not compensate during measurement.

FIG. 5 thus represents the plot of the beams when analyzing the aberrations of a short-sighted eye. On this diagram, for clarity purposes, solely the test and illumination paths are represented, but the assembly is the same as in the example of FIG. 1A. In this example, taking into account the fact that the eye is short-sighted, the 'back' analysis beam FA converges globally at the output of the eye. As described above, the analysis means of the wave-front enable to determine the value of the displacement of the platform PTF1 for conjugating the retina of the eye RET with the filtering hole FLT by the lens L1. In practice, the displacement value Dep (the positive direction is indicated by an arrow on the measurement axis z) of the platform PTF1 relative to the ametropia of the eye (in dioptry) is:

$$Dep = -f_1^2 \times D$$

Where $f_1$ is the focal distance of the lens L1.

In the example of a short-sighted eye, the platform PTF1 is brought closer to the lens L1.

FIG. 5 enables to underline the elimination of the stray reflections thanks to the device according to the invention. The assembly represented is identical to that of FIG. 1A. Indeed, the implementation of an illumination beam FE off-centre with respect to the measurement z in association with the filtering hole as described, enables very efficient elimination not only of the stray reflections on the cornea (reflections noted $REF_c$ on FIG. 5) but also of the stray reflections on the imaging means L1 (reflections noted $REF_L$ on FIG. 5), and this without any losses of the flux useful for analysis.

It should be noted that the device according to the invention also enables to get rid of the stray reflections of any diopter placed between the eye and the filtering element FLT, and in particular, glass lenses, as illustrated on FIG. 6. Indeed, the glass lenses (VER) are in the form of two vaulted diopters, the stray reflections (noted $REF_D$ on FIG. 6) are therefore stopped by the filtering hole FLT in the same way as the other stray reflections. This enables to test the eye of a patient wearing his corrective lenses and thereby to check all the aberrations of the eye system and corrective lenses, which constitutes a significant advantage of the device according to the invention. On the assembly of FIG. 6, it can be noted that the platform PTF1 is again in '0 dioptry' position since the corrective lenses enable to correct myopia.

Thanks to its performances as regards the suppression of stray reflections, the device according to the invention enables moreover to test an artificial eye-type system wherein the quality of an implant should be tested, for example. Indeed, in such a system, the stray reflections are increased because of a larger number of air/matter interfaces (in a living eye, the stray reflection occurs mainly on the cornea).

The device according to the invention also enables to measure the topography of the anterior face of the cornea COR of the eye, with all the advantages aforementioned. This measurement enables in particular to know with precision the portion of the shape of the anterior surface of the cornea in the aberrations of the eye. It also enables to control this surface, for example in ocular surgery for correction of the vision. Two assembly examples enabling such measurement are illustrated on FIGS. 7 and 8.

FIG. 7 shows an assembly which is substantially similar to that of FIG. 1A. However, the illumination path comprises moreover means for transmitting an illumination beam $FE_c$ centred on the measurement axis z, of predetermined diameter, converging at the centre of the filtering element FLT. In practice, it may be a beam emitted by the same source SRC as in the example of FIG. 1A, but the diaphragm APT has been withdrawn in order to centre the illumination beam and to enlarge its diameter. To measure the topography of the cornea, the position of the platform PTF1 is adjusted along the measurement axis z (in practice, the platform is at a certain distance) in order to guarantee substantially the optical conjugation by the imaging means L1 of the curvature centre of the cornea with the centre of the filtering element FLT, thereby enabling self-collimation of the illumination beam on the anterior face of the cornea. The flux FA reflected on said face is then sent towards the analysis means MA in order to carry out the measurement. This configuration requires working with a short focal and wide aperture lens L1, as well a significant displacement range for the platform PTF1. The optical path between the filtering element and the lens L1 can also be increased by dint of a set of 3 mirrors or more.

In the variation illustrated on FIG. 8, these constraints are avoided by adding an additional self-collimation system ATC between the lens L1 and the eye EYE, whereby this system is interdependent upon the imaging means L1. The self-collimation system enables to focus the illumination beam $FE_C$ at the curvature centre of the cornea, the flux reflected on the anterior face of the cornea being sent towards the analysis means MA in order to measure the topography of the cornea.

The other features of the assemblies of FIG. 7 or 8 are identical to those of the assembly of FIG. 1A. Notably, the illumination beam $FE_C$ is focused thanks to the lens L3 at the centre of the filtering element FLT, then captured by the lens whereof a focus is substantially confused with the centre of the filtering element. The illumination beam $FE_C$ arrives substantially collimated on the self-collimation system ATC. Said beam is calculated for a 'standard' cornea, of given curvature radius so that the illumination beam incident on said standard cornea converges at the centre of curvature of the cornea, the beam FA reflected on the cornea (corresponding to the 4% reflection approximately) being then confused with the incident beam FE. The beam FA is then analysed as previously by the analysis means MA in order to determine the phase of the wave-front reflected by the cornea, which enables to calculate its shape parameters and to plot a map thereof. It is necessary, as when measuring all the aberrations of the eye, to ensure conjugation between a predetermined plane of the eye (the plane of the pupil or advantageously, the plane tangent to the apex of the cornea) and the analysis plane PA. To do so, eye-positioning means may be used as described above, by using the imaging path VI. The platform 1, the lens L1 and the self-collimation system ATC move as a unit along the measurement axis z until, for instance, the image of the pupil is clear on the imaging camera IMA. If the cornea is 'standard', the analysis beam FA comes out in parallel beams from the self-collimation system, it is focused at the centre of the filtering hole by L1, then is sent towards the analysis means MA by the blade LM1 where it is incident in flat waves. If the cornea shows a deviation in the curvature radius with respect to a standard cornea, said deviation is measured by the analysis means. Very accurate measurement of the curvature radius is possible by moving the platform PTF1 on either side of the position for which the analysis beam is incident on the flat wave analysis beams. For this measurement, the stray reflections on the imaging means are far less critical. Indeed, the reflection on the cornea generates a light flux which is far greater than the diffusion on the retina of the eye and an antiglare process on the imaging means suffices to limit the effect of the stray reflections, although the illumination beam is not off-centre.

The invention claimed is:

1. A device for measuring the aberrations in an eye-type system, comprising an illumination path with notably means for transmitting an illumination beam (FE) to form by backscattering on the retina of the eye a secondary light source and a test path with notably test means in a given test plane (PA) of the phase of the wave emitted by said secondary source and emerging from the eye, characterised in that it comprises moreover:

imaging means (L1) and eye-positioning means enabling in particular to position a predetermined plane of the eye in a focal plane of said imaging means,
    a stray reflection filtering element (FLT) whereof the centre defines with the optical centre of the imaging means (L1) a measurement axis (z), substantially centred on the pupil of the eye,
    optical separation means (LM1) placed on the measurement axis and defining the illumination path and the test path,
    on the illumination path, an illumination diaphragm, of predetermined aperture,
    optical conjugation means (L2, L3) centred on the measurement axis and enabling optical conjugation between said predetermined plane of the eye, the plane of the illumination diaphragm and the test plane,
    and characterised in that the illumination beam converges substantially at the centre of the filtering element (FLT), in that the filtering element, the illumination path, the test path, the separation means and the conjugation means are interdependent, placed on a platform (PTF1) mobile relative to the imaging means (L1) along the optical axis of said means (z), enabling adjustment, with respect to the ametropia of the eye, of the optical conjugation by said means (L1) of the retina of the eye with the centre of the filtering element, and in that the illumination diaphragm is off-centre with respect to the measurement axis, so that the stray light flux reflected by the cornea of the eye, the imaging means (L1) as well as any diopter situated between the filtering element and the cornea, is deflected from the test path by the filtering element (FLT).

2. A device according to claim 1, characterised in that the filtering element (FLT) is composed of a drilled opaque blade, the hole being centred on the measurement axis (z), of predetermined dimensions so that the illumination beam (FE) and the test beam (FA) focused substantially at the centre of said hole, are transmitted by the filtering element whereas the stray reflections are stopped by the opaque portion of the filtering element.

3. A device according to claim 1, characterised in that the filtering element (FLT) is virtual, formed by the image of an actual filtering element FLTO, said actual filtering element (FLTO) being placed on the test path VA.

4. A device according to claim 3, characterised in that the actual filtering element (FLTO) is formed of a drilled opaque blade.

5. A device according to claim 2, characterised in that the size of the hole of the opaque blade is controllable.

6. A device according to claim 1, characterised in that the filtering element (FLT) is composed of a drilled mirror, the hole being centred on the measurement axis (z), of predetermined dimensions so that the illumination beam (FE) and the test beam (FA) focused substantially at the centre of said hole, are transmitted by the filtering element whereas the stray reflections are deflected by the reflecting portion of the filtering element.

7. A device according to claim 1, characterised in that the filtering element (FLT) comprises a mirror centred on the measurement axis, of predetermined dimensions so that the illumination beam (FE) and the test beam (FA) focused substantially at the centre of said mirror, are reflected by the filtering element whereas the stray reflections are not deflected by said element.

8. A device according to claim 1, characterised in that it comprises moreover means (COM) for controlling said platform (PTF1), connected to the test means, causing a displacement along the measurement axis (z) of the platform according to a predetermined function of the ametropia of the eye measured by said test means.

9. A device according to claim 1, characterised in that said eye-positioning means comprise notably an imaging path (VI) of the pupil of the eye (PO), with a lens (L4) substantially centred on the measurement axis (z) and an imaging camera interdependent upon said platform (PTF1) comprising a detector situated on a focal plane of said lens (L4) and a display system.

10. A device according to claim 9, characterised in that the positioning means comprise moreover an illumination device of the eye formed of a set of light sources, whereas the position can be adjusted by tuning the image of said sources reflected by the cornea on the detector, thereby enabling to control the position of the plane tangent to the apex of the cornea of the eye.

11. A device according to claim 9, characterised in that the positioning means comprise moreover a quasi-punctual light source, centred on the measurement axis (z), and placed substantially at the focus of said lens (L4), a mask formed of at least two apertures whereof at least one is off-centre with respect to the measurement axis, and located near said source, to form at least two light beams, a separating blade receiving said beams, the position being adjusted by controlling on the detector of the imaging path, the superimposition of the spots formed by the beams after reflection on the cornea of the eye, thus enabling controlled positioning of the plane tangent to the apex of the cornea of the eye.

12. A device according to claim 9, characterised in that the eye-positioning means comprise moreover on the display of the detector of the imaging path, means for tracking the lateral position of the pupil of the eye, enabling to adjust this lateral position with respect to the position of the illumination beam relative to the size of the pupil.

13. A device according to claim 9, characterised in that said positioning means comprise moreover means for moving the imaging means (L1) and the platform (PTF1), interdependently, in order to adjust the position of the eye.

14. A device according to claim 1, characterised in that the optical conjugation means comprise imaging means (L2) on the test path, the test plane being confused with a focal plane of said imaging means, and imaging means (L3) on the illumination path, the plane of the illumination diaphragm being confused with a focal plane of said imaging means, said means (L3) also focusing the illumination beam at the centre of the filtering element (FLT).

15. A device according to claim 1, characterised in that the separation means comprise at least a first separating blade (LM1), substantially with flat and parallel faces, tilted on the measurement axis (z), crossed by a portion of the illumination beam and reflecting a portion of the wave emerging from the eye towards the test path.

16. A device according to claim 15, characterised in that the reflection coefficient of said blade (LM1) is greater than approximately 70%.

17. A device according to claim 15, characterised in that the thickness of said blade (LM1) introduces on the illumination beam, a predetermined offset with respect to the measurement axis (z), so that failing said blade accidentally, the illumination beam does not go through the filtering element any longer.

18. A device according to claim 1, characterised in that it comprises moreover a fastening path, enabling to fix the direction of the patient's gaze whereof the eye is tested, and including an illuminated image and a lens (L5), the lens conjugating substantially optically the image with the filtering element (FLT).

19. A device according to claim 1, characterised in that the test means comprise a Shack-Hartmann type wave-front analyser including notably a matrix of microlenses, a matrix detector, processing means, and the test plane corresponding to the plane of the microlens matrix.

20. A device according to claim 1, characterised in that the illumination path comprises moreover means for transmitting an illumination beam centred on the measurement axis (z), of predetermined diameter, converging at the centre of the filtering element (FLT), and in that the position of the platform (PTF1) is adjusted along the measurement axis (z) for substantially optical conjugation by the imaging means (L1) of the curvature centre of the cornea with the centre of the filtering element (FLT), enabling self-collimation of said illumination beam on the anterior face of the cornea, the flux reflected on said face being sent towards the test means (MA) in order to measure the topography of the cornea.

21. A device according to claim 1, characterised in that the illumination path comprises moreover means for transmitting an illumination beam centred on the measurement axis (z), of predetermined diameter, converging at the centre of the filtering element (FLT), and in that the imaging means comprise an additional and removable self-collimation system, enabling to focus said illumination beam (FE) at the curvature centre of the cornea, the flux reflected on the anterior face of the cornea being sent towards the test means (MA) in order to measure the topography of the cornea.

* * * * *